(12) United States Patent
Fitzgerald et al.

(10) Patent No.: US 11,065,445 B2
(45) Date of Patent: Jul. 20, 2021

(54) TRANSCRANIAL STIMULATION WITH REAL-TIME MONITORING

(71) Applicant: MONASH UNIVERSITY, Clayton (AU)

(72) Inventors: Paul B Fitzgerald, Clayton (AU); Caley M. Sullivan, Clayton (AU); Richard H. Thomson, Clayton (AU)

(73) Assignee: Monash University, Clayton (AU)

( * ) Notice: Subject to any disclaimer, the term of this patent is extended or adjusted under 35 U.S.C. 154(b) by 33 days.

(21) Appl. No.: 16/092,989

(22) PCT Filed: Apr. 10, 2017

(86) PCT No.: PCT/AU2017/050314
§ 371 (c)(1),
(2) Date: Oct. 11, 2018

(87) PCT Pub. No.: WO2017/177264
PCT Pub. Date: Oct. 19, 2017

(65) Prior Publication Data
US 2019/0134395 A1    May 9, 2019

(30) Foreign Application Priority Data
Apr. 11, 2016 (AU) .............................. 2016901342

(51) Int. Cl.
*A61N 1/36* (2006.01)
*A61B 5/00* (2006.01)
(Continued)

(52) U.S. Cl.
CPC .......... *A61N 1/36031* (2017.08); *A61B 5/369* (2021.01); *A61B 5/375* (2021.01);
(Continued)

(58) Field of Classification Search
CPC ............ A61N 1/36031; A61N 1/36025; A61N 1/0476; A61B 5/4064; A61B 5/0476;
(Continued)

(56) References Cited

U.S. PATENT DOCUMENTS

| 8,958,882 B1 | 2/2015 | Hagedorn |
| 2007/0142874 A1* | 6/2007 | John ...................... A61N 2/006 607/45 |

(Continued)

FOREIGN PATENT DOCUMENTS

WO     2015063127 A1    5/2015

OTHER PUBLICATIONS

International Search Report, Application No. PCT/AU2017/050314, dated May 15, 2017, 10 pages.
(Continued)

*Primary Examiner* — Gary Jackson
*Assistant Examiner* — Alexander M Eisenberg
(74) *Attorney, Agent, or Firm* — Ziegler IP Law Group, LLC

(57) ABSTRACT

Closed-loop transcranial stimulation and monitoring is disclosed that includes generating a stimulation signal having a set of first oscillation parameters; applying the stimulation signal transcranially to a patient; monitoring the stimulation signal as applied to the patient; receiving a brain activity signal from the patient; generating a feedback signal based on the monitored stimulation signal as applied to the patient; and generating a modified activity signal by subtracting the feedback signal from the brain activity signal; determining one or more second oscillation parameters of the modified activity signal; and adjusting the set of first oscillation parameters of the stimulation signal based on the one or more second oscillation parameters of the modified activity signal. Closed-loop transcranial stimulation and monitoring
(Continued)

is also disclosed in which the patient is engaged in a cognitive task.

20 Claims, 11 Drawing Sheets

(51) Int. Cl.
  *A61B 5/369* (2021.01)
  *A61B 5/375* (2021.01)
  *A61N 1/04* (2006.01)
  *A61B 5/318* (2021.01)
  *A61B 5/389* (2021.01)
(52) U.S. Cl.
  CPC .......... *A61B 5/4064* (2013.01); *A61B 5/4836* (2013.01); *A61B 5/7203* (2013.01); *A61N 1/36025* (2013.01); *A61B 5/0042* (2013.01); *A61B 5/318* (2021.01); *A61B 5/389* (2021.01); *A61B 5/6814* (2013.01); *A61N 1/0476* (2013.01)
(58) Field of Classification Search
  CPC ... A61B 5/7203; A61B 5/4836; A61B 5/0482; A61B 5/0042; A61B 5/6814; A61B 5/0402; A61B 5/0488
  USPC .......................................................... 607/45
  See application file for complete search history.

(56) References Cited

U.S. PATENT DOCUMENTS

| | | | |
|---|---|---|---|
| 2007/0265489 A1* | 11/2007 | Fowler | A61N 1/36082 600/12 |
| 2009/0082690 A1 | 3/2009 | Phillips et al. | |
| 2014/0324118 A1 | 10/2014 | Simon et al. | |
| 2015/0297108 A1 | 10/2015 | Chase et al. | |
| 2016/0038049 A1* | 2/2016 | Geva | A61N 1/36135 600/544 |
| 2017/0216593 A1* | 8/2017 | Lee | A61N 1/0492 |

OTHER PUBLICATIONS

European Patent Office, Extended European Search Report, Application No. 17781631.1, dated Mar. 31, 2020, 7 pages.

* cited by examiner

US 11,065,445 B2

TRANSCRANIAL STIMULATION WITH REAL-TIME MONITORING

CROSS-REFERENCE TO RELATED APPLICATION

The present application claims priority to Australian provisional patent application no. 2016901342 filed on 11 Apr. 2016, the content of which is hereby incorporated by reference.

TECHNICAL FIELD

The present disclosure relates to methods and apparatus for transcranial stimulation of brain activity.

BACKGROUND

Transcranial stimulation approaches are increasingly being investigated for their potential to improve mood and cognitive functions, with a widely investigated form being transcranial electrical stimulation and more specifically transcranial direct current stimulation (tDCS). tDCS involves the application of a weak electrical current applied to the scalp using two surface electrodes (anode and cathode) which has been shown to improve an increasing array of cognitive functions, including memory, attention, learning, and problem solving.

Although less common, transcranial alternating current stimulation (tACS) has also been investigated. While tDCS delivers an electrical current which travels in a constant unipolar direction, tACS delivers a current that alternates at a specified frequency back and forth between the electrodes. Stimulation with tACS in the EEG range (conventionally: 0.1-80 Hz) is believed to directly modulate cortical oscillations, with a growing number of studies showing entrainment of endogenous oscillations at the frequency of stimulation. The ability of tACS to entrain endogenous oscillations at the frequency of stimulation is significant as it allows for more direct enhancement of processes underlying cognition.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

The present disclosure generally provides methods and apparatus for performing transcranial stimulation that involve, e.g. as part of a closed-loop technique, receiving a brain activity signal from a patient; determining one or more oscillation parameters of the brain activity signal; generating a stimulation signal, the stimulation signal having one or more oscillation parameters based on the determined oscillation parameters of the brain activity signal; and applying the generated stimulation signal transcranially to the patient.

In one aspect, for example, the present disclosure provides a method of performing transcranial stimulation comprising:

generating a stimulation signal having a set of first oscillation parameters;
applying the stimulation signal transcranially to a patient;
monitoring the stimulation signal as applied to the patient;
receiving a brain activity signal from the patient;
generating a feedback signal based on the monitored stimulation signal as applied to the patient; and
generating a modified activity signal by subtracting the feedback signal from the brain activity signal;
determining one or more second oscillation parameters of the modified activity signal; and
adjusting the set of first oscillation parameters of the stimulation signal based on the one or more second oscillation parameters of the modified activity signal.

In another aspect, the present disclosure provides apparatus for performing transcranial stimulation, the apparatus comprising circuitry configured to:

generate a stimulation signal having a set of first oscillation parameters;
apply the stimulation signal transcranially to a patient;
monitor the stimulation signal as applied to the patient;
receive a brain activity signal from the patient;
generate a feedback signal based on the monitored stimulation signal as applied to the patient; and
generate a modified activity signal by subtracting the feedback signal from the brain activity signal;
determine one or more second oscillation parameters of the modified activity signal; and
adjust the set of first oscillation parameters of the stimulation signal based on the one or more second oscillation parameters of the modified activity signal.

The circuitry may comprise two or more electrodes placed on the scalp of the patient that are used to receive the brain activity signal. The received brain activity signal may be an electrical signal. The circuitry may comprise an electroencephalography (EEG) device and therefore the received brain activity signal may be in the form of an EEG signal. Other detectable oscillating activity signals can include but are not limited to signals, or a combination of signals, obtained using Near infrared spectroscopy (NIRS), Magnetoencephalography (MEG), Electromyography (EMG), Electrocardiography (ECG) and/or Functional magnetic resonance imaging (fMRI).

The stimulation signal may have any arbitrary waveform, e.g. the stimulation signal may be sinusoidal, square-wave, sawtooth, triangle-wave or otherwise. The stimulation signal may be an oscillating stimulation signal such as a transcranial alternating current signal (tACS) or another type of stimulation signal that can be applied transcranially to stimulate neurons in the brain. For example, as one alternative, the stimulation signal may be a transcranial magnetic stimulation signal (tMS) waveform. The magnetic stimulation may be provided as magnetic pulses and/or an alternating magnetic field. A combination of different stimulation signals may also be employed, such as a combination of electrical and magnetic signals.

The circuitry may be adapted to apply the stimulation signal transcranially to the patient via two or more electrodes, which may be the same electrodes as used to receive the brain activity signal or different electrodes. However, other application approaches may be taken. For example, where the stimulation signal is a tMS signal, it may be applied transcranially using a coil that locates adjacent the patient's scalp.

In the above aspects, the stimulation signal can be applied to the patient while the brain activity signal of the patient is being received and processed. The method and apparatus can therefore provide closed-loop control. The method and apparatus may provide 'real-time', closed-loop control in which the stimulation signal is continuously applied and adjusted in accordance with oscillation parameters identified in a brain activity signal and more particularly the modified brain activity signal.

In general, the received brain activity signal can be considered to be contaminated by the stimulation signal applied concurrently to the brain (i.e. it includes an artefact that is based on the stimulation signal). With a view to removing this contamination or otherwise, a feedback signal is generated based on monitoring of the stimulation signal as applied to the patient. The feedback signal may also be based on some or all of the set of first oscillation parameters. The monitoring may include monitoring of one or more properties of the stimulation signal as applied to the patient. Additionally, or alternatively, the monitoring may comprise extracting a portion of the stimulation signal, as applied to the patient. The monitoring may be carried out at least partly by a processor.

By subtracting the feedback signal from the brain activity signal, which feedback signal is based on the monitored stimulation signal as applied to the patient, the artefact may be removed more precisely or completely. This may contrast with artefact removal by subtraction of a signal, from the brain activity signal, that is based only on the first set of oscillation parameters of the signal as generated (or intended to be generated). By removing the artefact in the manner described herein, the modified activity signal can be determined as a signal that is more closely aligned with the endogenous oscillating activity signals in the brain of the patient. Having isolated this modified activity signal, one or more second oscillation parameters of the modified activity can be determined, which second oscillation correspond to endogenous oscillation parameters, and one or more of the first oscillation parameters of the stimulation signal can be adjusted accordingly.

The feedback signal may be subject to one or more processing steps prior to its subtraction from the brain activity signal. For example, the feedback signal may be subject to conditioning to align its phase or amplitude with the brain activity signal or otherwise. Appropriate signal conditioning techniques known in the art may be carried out in this regard.

By monitoring the stimulation signal as applied to the patient, the actual nature of the stimulation signal can be taken into account. In general, while the stimulation signal as generated might be a basic sinusoid, for example, when the stimulation signal is actually applied to the patient, the stimulation signal can change. If the stimulation signal is a transcranial alternating current signal (tACS), for example, the voltage of the stimulation signal may vary over time. This is because a tACS device is normally configured to deliver a constant current and therefore the voltage of the signal will vary as electrode impedance varies, for example. Electrode impedance may vary due to small changes in the quality of contact between the electrodes and the patient's scalp, or otherwise.

Thus, in one embodiment, the stimulation signal as applied to the patient may be monitored to determine and/or account for changes in the voltage and/or impedance and/or current waveform of the stimulation signal as applied to the patient. In some embodiments, the feedback signal may be constructed based on the first oscillation parameters of the generated stimulation signal but as adjusted in view of the monitoring of the stimulation signal as applied to the patient. In some embodiments, the feedback signal may be based on an extracted portion of the stimulation signal as applied to the patient. The portion may be extracted after the stimulation signal has been subjected to constant current control, for example, and optionally after being subjected to amplification.

As indicated, the circuitry to receive the brain activity signal from a brain of a patient may include two or more electrodes to receive an electrical activity signal from the brain transcranially. The circuitry may also include an amplifier to amplify the electronic activity signal received across the two or more of the electrodes. The circuitry may also include a first signal convertor (e.g., an analogue-to-digital-convertor (ADC)), which may be connected to the amplifier and may convert the electrical activity signal from an analogue to a digital signal. The circuitry may also include a processor, which may be connected to the first signal converter to receive the converted signal as brain activity signal for further processing.

The circuitry to generate and apply the stimulation signal may include the processor or a further processor. The processor may be connected to a second signal convertor (digital-to-analogue-convertor (DAC)) that creates an analogue version of the generated stimulation signal. A controlled current source may be provided that modulates the amplitude of the stimulation signal to control voltage levels of the signal and therefore maintain a constant current of the signal. The same or a further amplifier may be provided to amplify the signal to arrive at stimulation signal that is applied to the patient and which has a desired constant current level. The circuitry may include two or more electrodes to apply the stimulation signal to the brain transcranially. To monitor the stimulation signal as applied to the patient, a portion of the signal may be extracted, e.g. immediately prior to application to the patient, and delivered to the processor for monitoring.

The set of first oscillation parameters may comprise the frequency, phase and amplitude of the generated stimulation signal. The one or more second oscillation parameters that are determined may comprise any one or more of the frequency, phase and amplitude of the modified activity signal. For example, the second oscillation parameters may comprise at least the frequency of the modified activity signal. As another example, the second oscillation parameters may comprise at least the frequency and phase of the modified activity signal. While a basic stimulation signal may be used, in some embodiment more complex stimulation signals, e.g. employing AM or FM modulation, may be employed. In these embodiments, the first oscillation parameters and the second oscillation parameters may comprise one or more of the frequency, phase and/or amplitude of specific components of the complex signals, such as a modulating signal component and a carrier signal component or otherwise.

By determining a frequency of the modified activity signal, for example, a frequency of the stimulation signal can be adjusted to have the same frequency as the modified activity signal (and generally, therefore, the endogenous brain activity). This can provide for entrainment of the endogenous oscillations at the frequency of stimulation.

Similarly, by determining a phase of the modified activity signal, for example, a phase of the stimulation signal can be adjusted to have the same phase as or a desired phase-shift from, a determined phase of the modified activity signal. This can provide for intentional phase matching or mismatching of the endogenous oscillations with the phase of stimulation. For example, the phase of the stimulation signal can be adjusted to be in-phase with the determined phase of the modified activity signal. Alternatively, the phase of the stimulation signal can be adjusted to be out of phase (e.g. anti-phase) with the determined phase of the modified activity signal.

It is understood, for example, that fronto-parietal coupling of stimulation and neural activity signals in the theta band when in-phase (~0° relative phase) may be associated with recognition, encoding, short-term retention, and planning. In-phase synchronization can result in improved reaction times to the stimulation signal while out-of-phase desynchronization can result in a deteriorated performance. Nevertheless, out-of-phase desynchronization can still have valid therapeutic uses.

The brain activity signal and/or the modified activity signal may be filtered into and/or analysed in one or more frequency bands prior to determining the one or more second oscillation parameters. The one or more second oscillation parameters may be determined for at least one of the frequency bands.

The stimulation signal may comprise one or more frequency bands and adjusting the set of first oscillation parameters of the stimulation signal based on the one or more second oscillation parameters of the modified activity signal that are determined may comprise adjusting the set of first oscillation parameters in at least one frequency band that corresponds to a frequency band in which the second oscillation parameters were determined.

The frequency bands may comprise one or more of: delta frequency band (<about 4 Hz), theta frequency band (about 4 to 8 Hz), alpha frequency band (about 8 to 14 Hz), beta frequency band (>about 14 Hz) and sub-bands and overlapping bands thereof, including gamma frequency band (>about 30 Hz) and Mu frequency band (about 8 to 12 Hz), or otherwise.

As indicated, the oscillation parameters may comprise frequency and phase. Thus, an alpha frequency of the stimulation signal may be adjusted to have the same frequency and/or phase as an alpha frequency of the modified activity signal, or a theta frequency of the transcranial stimulation signal may be adjusted to have the same frequency and/or phase as theta frequency of the oscillating activity signal, etc.

Within one or more frequency bands of interest, the generation and adjusting of the stimulation signal may be optimised for a best fit with the endogenous brain activity of the patient, e.g., by having a corresponding frequency and/or phase to the modified activity signal. The generation of a stimulation signal with an appropriate fit may be carried out over a period of time, e.g. iteratively. For each iteration of a stimulation signal, a statistical index of the quality of fit may be calculated. Once the quality of fit is calculated to be sufficiently close and the stimulation signal is therefore generated, the method/apparatus may wait until the phase of the determined signal is aligned as desired with the endogenous oscillating signal and then a trigger may be provided, at that exact point in time, for the stimulation signal to be applied to the patient. The desired alignment of phase may be in-phase alignment or anti-phase alignment, for example. In-phase alignment of the stimulation signal with the endogenous activity offers a theoretically additive process potentially amplifying activity at a target frequency and/or region, while anti-phase alignment will suppress activity at the target frequency and/or region. The present disclosure may provide a method and apparatus for directly modulating and steering activation patterns of oscillatory activity in the brain towards a desired outcome such as modulating mood and/or behaviour.

By basing the frequency and/or phase of the first parameters of the stimulation signal on corresponding parameters of the modified activity signal from the patient, a bespoke, patient-specific stimulation strategy can be determined in a closed-loop, realtime, environment. The approach may provide for dynamic changes in the stimulation strategy by continuously cycling through the above steps over an extended period of time. The stimulation strategy may be carried out until a desired therapeutic outcome is realised or until a predetermined total time has elapsed or otherwise.

The approach of the present disclosure can account for different cognitive functions being associated with neuronal activity across multiple, different frequency bands, and account for the optimal 'pattern' of activity being dependent on the individual patient and changing over time. This can contrast with an approach where appropriate oscillation parameters for stimulation are determined 'off-line' and stimulation is provided in a fixed or static manner. The approach of the present disclosure can also provide for frequency-coupling between the stimulation signal and the endogenous oscillating activity of the patient in one or more frequency bands.

Where an EEG device is employed to receive a brain activity signal/monitor brain activity, the EEG device can collect EEG signals via bio-amplifiers, which signals are conditioned and optionally filtered, in real-time, into the frequency bands of interest.

In some embodiments the adjusting of the set of first oscillation parameters of the stimulation signal may be based on a modulation parameter, in addition to the one or more second oscillation parameters that are determined. The modulation parameter may be a chirp, for example. Thus, during application of the stimulation signal, the frequency of the stimulation signal may be increased (up-chirp) or decreased (downchirp). Chirping of the stimulation signal may be reflected in the oscillating activity signals of the brain due to neural entrainment, i.e. the oscillation parameters of the activity signals of the brain may adjust to synchronise with the changing parameters of the stimulation signal.

In some embodiments, an external input may be provided to control how the one or more second oscillation parameters are determined and/or how the stimulation signal is adjusted based on the one or more second oscillation parameters. Controlling how the one or more second oscillation parameters are determined may comprise controlling which one or more second oscillation parameters are determined and/or when the one or more second oscillation parameters are determined. The external input may be provided based on a task provided to the patient and/or based on an external observation of the patient's behaviour or environment. Where the external input is based on a task, the external input may be based on the commencement of the task and/or the patient's approach to completing the task, for example. Where the external input is based on an external observation, the external input may be based on facial expressions or biologic parameters of the patient indicative of mood, for example. The external input may cause a particular portion of the modified activity signal to be targeted in order to identify the second oscillation parameters. The portion may be a specific time portion of the modified activity signal (e.g. corresponding to when the task was commenced or completed, etc.) and/or a portion having particular parameters, e.g. falling within a particular frequency band, for example.

The external input may be provided by an external device such as personal computing device, e.g., a smartphone or tablet, or other computing devices such as virtual or augmented reality devices. The external device may be configured to communicate with the processor of the apparatus via wire or wirelessly, e.g., via Bluetooth® or WiFi®. The external device may set tasks for the patient, monitor completion of the tasks, and/or provide an external observation of the patient or the patient's environment.

Thus, cognitive tasks, sensory stimuli, or combinations thereof may be incorporated in the control loop or loops of the present disclosure, whereby performance on or an activated response to certain activities or events, for example, are used to inform and manipulate the generation of parameters of the stimulation signal. Due to the closed loop nature of the approach, endogenous activity can therefore be directly modulated during the execution of a specific task, by a specific individual towards optimal performance, for example.

Following from the discussions above, in one aspect, the present disclosure provides a method of performing transcranial stimulation comprising:

generating a stimulation signal having a set of oscillation parameters;
applying the stimulation signal transcranially to a patient;
engaging the patient in a cognitive task:
receiving a brain activity signal from the patient;
monitoring a response of the patient to carrying out the task;
removing an artefact from the brain activity signal that is based on the stimulation signal, to obtain a modified activity signal;
analysing the modified activity signal;
adjusting the oscillation parameters of the stimulation signal as applied to the patient based on the monitored response of the patient to carrying out the task and the analysis of the modified activity signal.

Moreover, in another aspect, the present disclosure provides apparatus for performing transcranial stimulation, the apparatus comprising circuitry configured to:

generate a stimulation signal having a set of oscillation parameters;
apply the stimulation signal transcranially to a patient;
engage the patient in a cognitive task:
receive a brain activity signal from the patient;
monitor a response of the patient to carrying out the task;
remove an artefact from the brain activity signal that is based on the stimulation signal, to obtain a modified activity signal;
analyse the modified activity signal; and
adjust the oscillation parameters of the stimulation signal as applied to the patient based on the response of the patient to carrying out the task and the analysis of the modified activity signal.

In some embodiments, the analysis of the modified activity signal may be across two or more frequency bands of the modified activity signal. The adjustment of the oscillation parameters of the stimulation signal as applied to the patient may be different for different frequency bands of the stimulation signal.

The method and apparatus may employ any one or more features of the previously described aspects. For example, the artefact removal may be carried out by determining a feedback signal and subtracting that feedback signal from the brain activity signal, e.g. in accordance with discussions above. The feedback signal may be based in part on monitoring of the stimulation signal as actually applied to the patient. Nevertheless, alternative artefact removal techniques may be employed in order to allow real-time brain monitoring and stimulation to take place.

The monitoring of the response of the patient to carrying out the task may be based at least partly on the analysis of the modified activity signal. Additionally, or alternatively, the task results derived from a particular behaviour or reaction of the patient to carrying out the task may be received and the monitoring of the response of the patient to carrying out the task may be based at least partly on an analysis of the received task results.

Task results may be obtained by active and/or passive monitoring of the patient in response to the task. Passive behaviour may be monitored by making an external observation of the patient's behaviour or environment, e.g. by monitoring facial expressions or biologic parameters of the patient indicative of mood, for example. Active behaviour may be monitored by recording deliberate reactions from the patient, e.g. that are inputted to the external device that presents the task to the patient, or to one or more additional devices.

The task presented to the patient may be modulated, at least in part, on the basis of the results of the task. Additionally, or alternatively, the task presented to the patient may also be modulated, at least in part, on the basis of the monitored brain activity signal. Modulating of the task may comprise increasing the difficulty of the task, reducing the difficulty of the task, increasing an emotiveness of the task, decreasing an emotiveness of the task or otherwise.

The analysing the modified activity signal may comprise determining which regions or anatomical sites of the patient's brain generated some or all of components of the modified activity signal. The applying of the stimulation signal to the patient may comprise applying the stimulation signal to one or more of these regions or anatomical sites.

The adjustment of the oscillation parameters for different frequency bands of the stimulation signal may comprise adjusting the peak frequency in the frequency bands, e.g. to increase the peak frequency of the stimulation signal in one frequency band and decrease the peak frequency of the stimulation signal in another frequency band. In some embodiments, the adjustment of the oscillation parameters for different frequency bands may be carried out until a predetermined or dynamically determined level of performance to carrying out the task is achieved by the patient.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DESCRIPTION OF EMBODIMENTS

Embodiments of the present disclosure provide methods and apparatus for performing transcranial stimulation, including closed-loop arrangements. The methods and apparatus can involve, for example, receiving a brain activity signal from a patient, determining one or more oscillation parameters of the brain activity signal, generating a stimulation signal, the stimulation signal having one or more oscillation parameters based on the determined oscillation parameters of the brain activity signal, and applying the generated stimulation signal transcranially to the patient.

In embodiments of the present disclosure, the stimulation signal is applied to the patient while the brain activity signal of the patient is being received and processed. Continuous, 'real-time' monitoring and control can therefore be provided in which the stimulation signal is applied and adjusted in accordance with oscillation parameters identified in the brain activity signal. Thus, the brain activity signal, which provides information about endogenous brain activity, can be used to modify how the stimulation signal is applied to the patient, e.g., to ensure that the stimulation signal has properties matching properties of the endogenous brain activity, or otherwise.

A problem, however, is that the received brain activity signal is effectively contaminated by the stimulation signal applied concurrently to the brain. The brain activity signal can be considered to include an artefact that is based on the stimulation signal.

Figure 1:
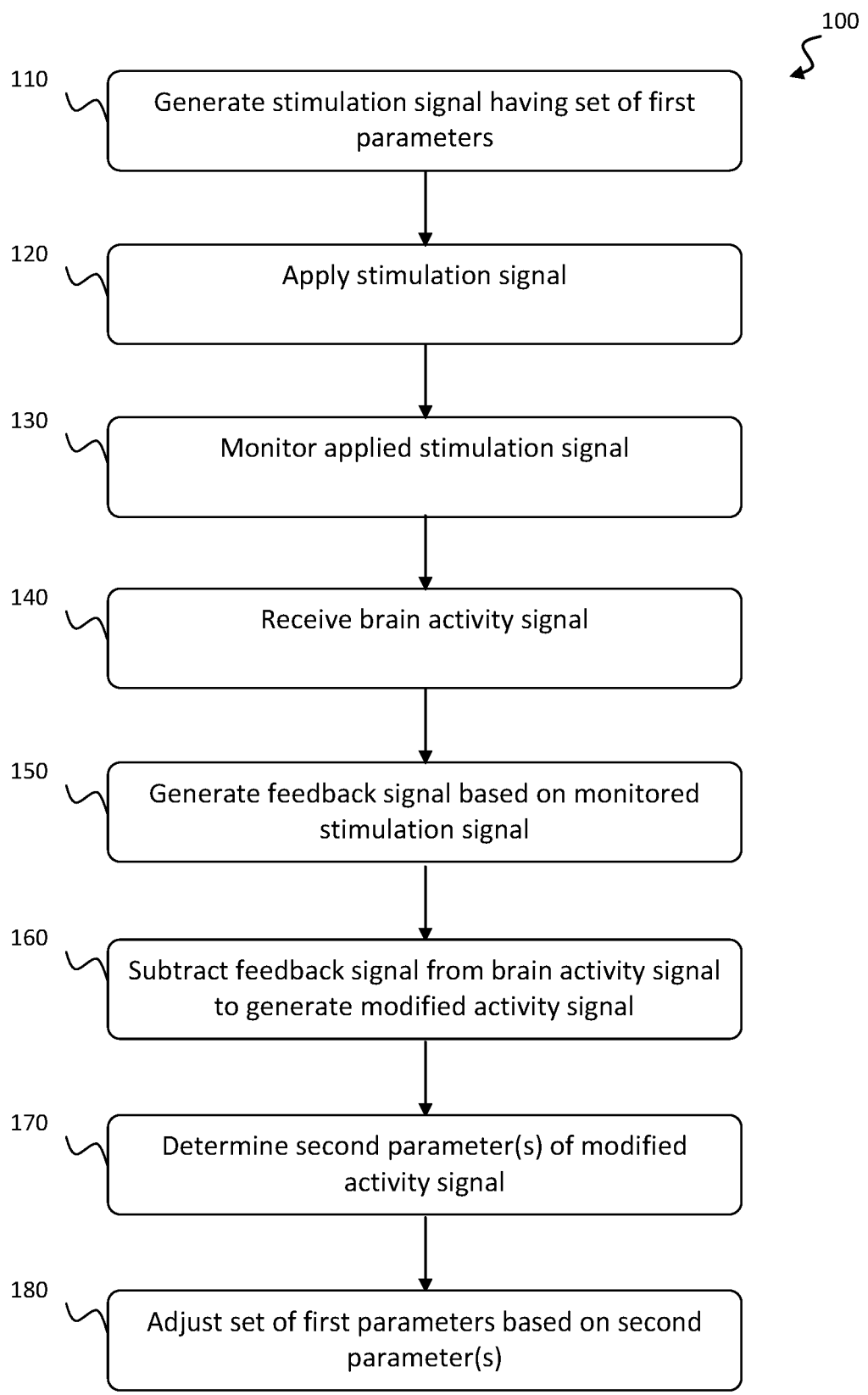
FIG. 1 is a flow chart illustrating a method of performing transcranial stimulation according to an embodiment of the present disclosure.

To address this and other problems, in one embodiment, a method of performing transcranial stimulation is carried in accordance with the features of the flow chart 100 illustrated in FIG. 1. At 110, a stimulation signal having a set of first oscillation parameters is generated. At 120, the stimulation signal is applied transcranially to a patient. At 130, the stimulation signal as applied to the patient is monitored. At 140, a brain activity signal from the patient is received. At 150, a feedback signal based on the monitored stimulation signal is generated. At 160, a modified activity signal is generated by subtracting the feedback signal from the brain activity signal. At 170, one or more second oscillation parameters of the modified activity signal are determined. At 180, one or more of the first oscillation parameters, of the set of first oscillation parameters of the stimulation signal, are adjusted based on the one or more second oscillation parameters of the modified activity signal.

By subtracting the feedback signal from the brain activity signal, which feedback signal is based on the monitored stimulation signal as applied to the patient, the modified activity signal can be substantially artefact-free and can therefore be more closely indicative of the endogenous oscillating activity in the brain of the patient. One or more second oscillation parameters of the modified activity can subsequently be determined, which second oscillation parameters can therefore correspond more closely to endogenous oscillation parameters, and the stimulation signal can be adjusted accordingly.

Figure 2:
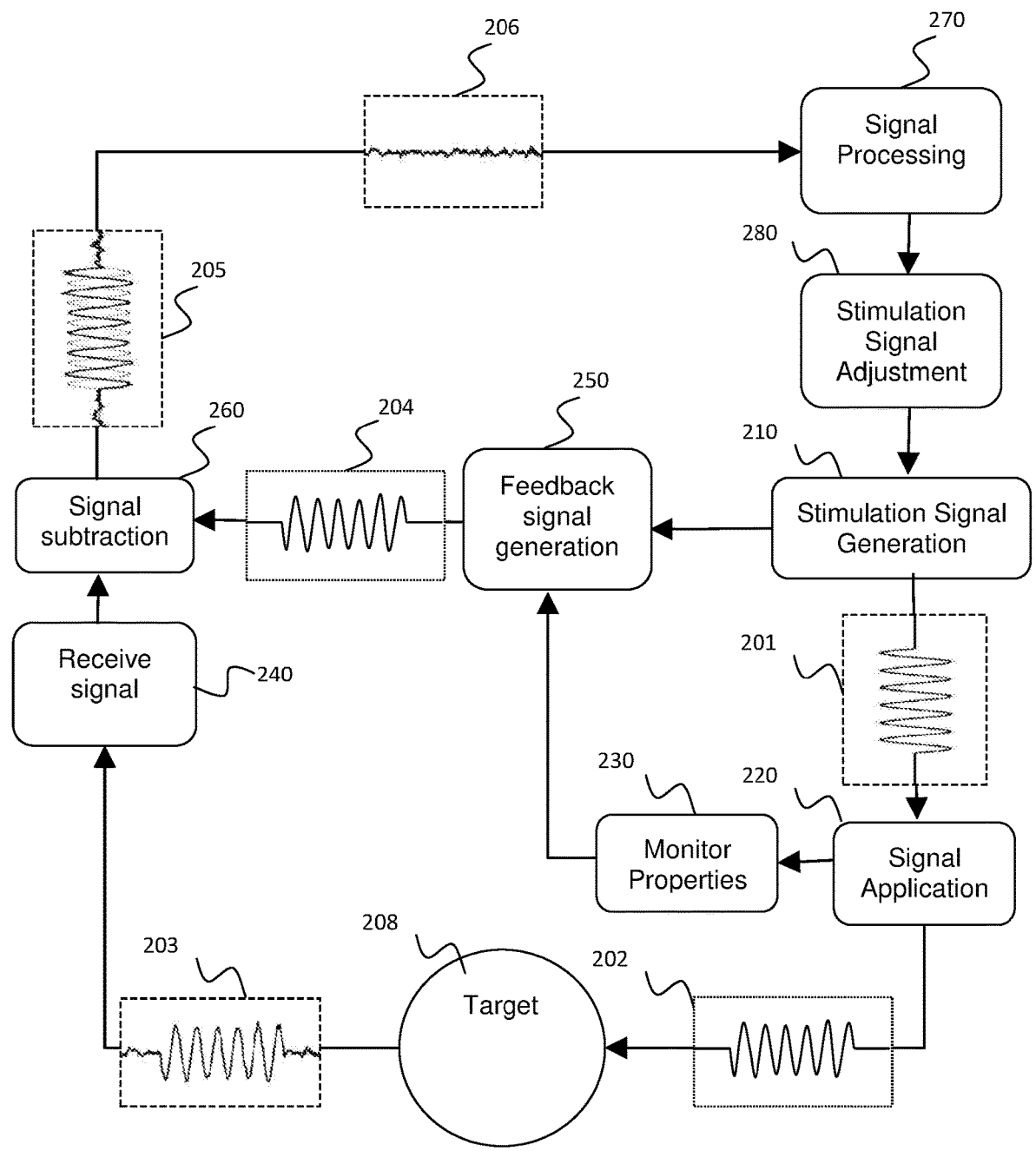
FIG. 2 is a schematic diagram of the method of FIG. 1.

FIG. 2 provides a schematic diagram of the method described above, and illustrates the method as a continuous loop in which a further feedback loop is provided. At 210, the stimulation signal is generated, which stimulation signal has a set of first oscillation parameters and can have a waveform generally as indicated in box 201. At 220, the stimulation signal is applied transcranially to a target (a patient) 208. When the stimulation signal is actually applied to the patient, it can be different from the stimulation signal as generated, as discussed in more detail below. For example, it may have a waveform as indicated in box 202. At 230, the stimulation signal as applied to the patient is monitored. At 240, a brain activity signal from the target is received. The brain activity signal may have a waveform as illustrated in box 203, which is substantially a combination of the stimulation waveform 202 and endogenous waveforms in the brain. At 250, a feedback signal based at least on the monitored stimulation signal as applied to the patient, and optionally also information about the set of first oscillation parameters, is generated. The feedback signal may have a waveform as indicated in box 204. At 260, a modified activity signal is generated by subtracting the feedback signal from the brain activity signal. The application of a subtraction waveform is illustrated in box 205 and the result is a modified activity signal having a waveform as illustrated in box 206. At 270, by virtue of signal processing techniques, one or more second oscillation parameters of the modified activity signal are determined. At 280, the set of first oscillation parameters of the stimulation signal are adjusted based on the one or more second oscillation parameters of the modified activity signal. Thus an adjusted stimulation signal can then be generated at 210 that is based on features of the modified activity signal, which in turn correspond to features of the endogenous brain activity.

By monitoring the stimulation signal as applied to the patient, the actual nature of the applied stimulation signal can be taken into account. In general, while the stimulation signal as generated might be a known signal such as a basic sinusoid, when the stimulation signal is actually applied to the patient, the stimulation signal can change.

In one embodiment, the stimulation signal is a transcranial alternating current signal (tACS). The voltage of a tACS stimulation signal as applied to the patient can vary over time if the tACS signal is delivered in a constant current mode. To maintain a constant current, the voltage can vary as electrode impedance varies, for example. Electrode impedance may vary due to small changes in the quality of contact between the electrodes and the patient's scalp, or otherwise. Thus, one or more properties of the (tACS) stimulation signal as applied to the patient may be monitored, which properties can comprise the voltage of the stimulation signal as applied to the patient, for example.

Figure 3A:
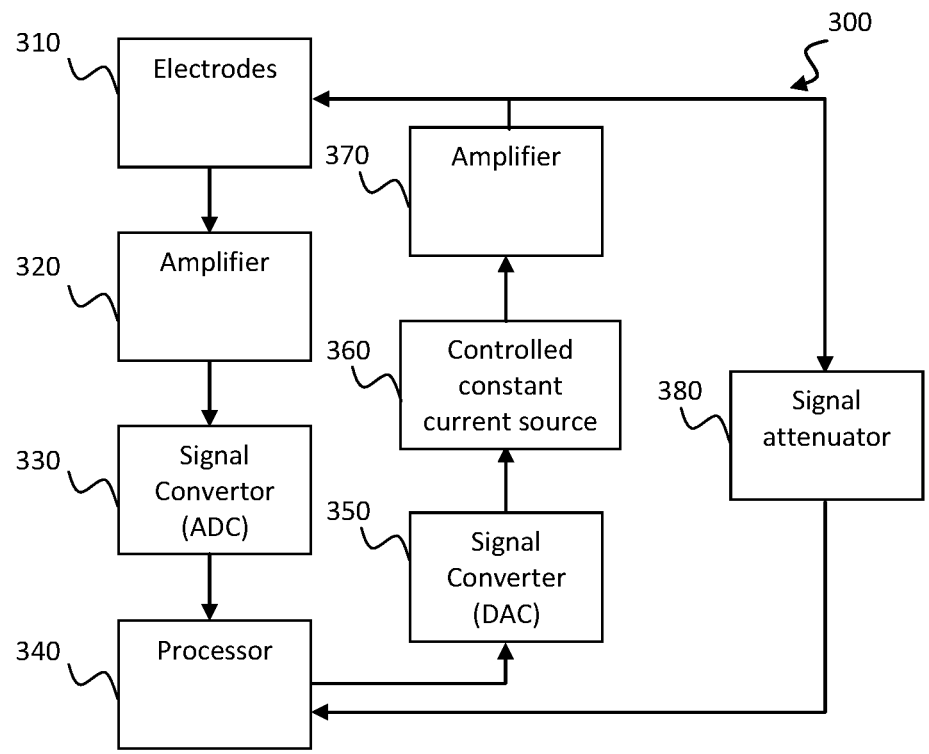
FIG. 3a is a schematic diagram of apparatus for performing transcranial stimulation in accordance with an embodiment of the present disclosure.

A schematic diagram of apparatus 300 for performing transcranial stimulation according to an embodiment of the present disclosure is illustrated in FIG. 3a. The apparatus 300 includes circuitry configured to receive the brain activity signal from a brain of a patient, and includes a plurality of electrodes 310 that locate on the scalp of a patient to receive an electrical activity signal of the brain transcranially, an amplifier 320 adapted to amplify the electronic activity signal received across two or more of the electrodes 310, a first signal convertor (analogue-to-digital-convertor (ADC)) 330 connected to the amplifier 320 to convert the electronic activity signal from analogue to digital, and a processor 340 connected to the first signal converter 330 and adapted to receive the converted signal as brain activity signal for further processing. In this embodiment, the approach to receive the brain activity signal is generally in accordance with principles of electroencephalography (EEG) and thus the components may be provided at least in part by an EEG device.

The processor 340 is also configured to generate a stimulation signal, which signal is applied to the brain of the patient via two or more electrodes of the plurality of electrodes 310. The processor 340 is connected to a signal convertor (digital-to-analogue-convertor (DAC)) 350 that creates an analogue version of the generated stimulation signal of a desired phase and frequency. The amplitude of the analogue signal is modulated by a controlled constant current source 360 that controls voltage levels of the signal and therefore maintains a constant current of the signal. The signal is amplified by an amplifier 370 to arrive at the stimulation signal as applied to the patient, and which has a desired constant current level. A portion of the signal as applied to the patient is extracted and delivered, via a signal attenuator 380, to the processor, allowing the processor 340 to monitor the stimulation signal as applied to the patient and determine a feedback signal for artefact removal on this basis. The monitoring of the stimulation signal may comprise actively determining one or more properties of the signal as applied to the patient and generating the feedback signal on this basis, optionally in conjunction with knowledge of the first oscillation parameters of the stimulation signal as generated. Alternatively, the monitoring may comprise mere receiving of the extracted signal, the feedback signal being based on the extracted signal (subject to further conditioning of the extracted signal or otherwise). The attenuator 380 may scale down the voltage so that it is in a similar range to the amplifier 320 and can be monitored by the processor simultaneously with the received brain activity signal (e.g. EEG signal). In this embodiment, the approach generating and applying the stimulation signal is based on principles of tACS and thus the components may be provided at least in part by a tACS device.

Figure 3B:
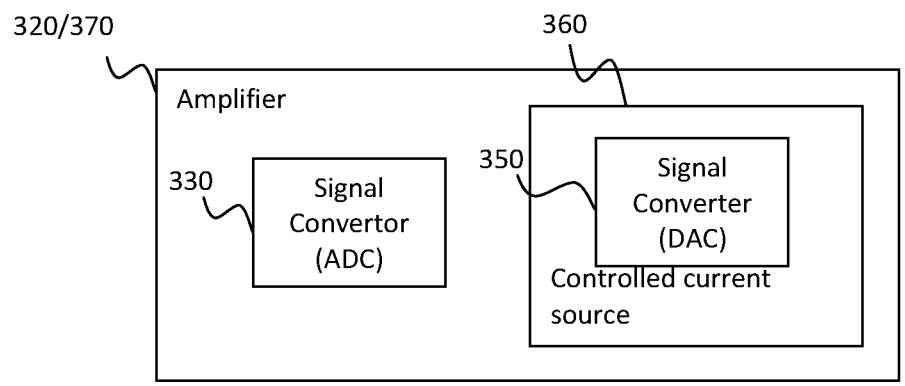
FIG. 3b is a schematic diagram of integrated components of the apparatus of FIG. 3a according to an embodiment of the present disclosure.

As indicated in FIG. 3b, in one embodiment the signal converters 330, 350 can be integrated with an amplifier unit 320/370 and the current control source 360.

In general, the apparatus 300, including the processor 340, can carry out the method described above. The processor 340, for example, can generate the stimulation signal having a set of first oscillation parameters, determine one or more properties of the stimulation signal as applied to the patient, receive the brain activity signal, generate the feedback signal based on the monitored properties of the stimulation signal, subtract the feedback signal from the brain activity signal, determine one or more second oscillation parameters of the modified activity signal and adjust the set of first oscillation parameters of the stimulation signal based on the one or more second oscillation parameters of the modified activity signal.

In accordance with discussions above, the stimulation signal as applied to the patient may be a signal that has been modulated following initial generation of the signal, due to changes in impedances at the electrode-skin interface or otherwise. The stimulation signal as applied to the patient may be the stimulation signal after being subjected to a constant current control, for example, and optionally also amplification.

The processor can comprise a digital signal processor (DSP) and/or other components and/or software modules to carry out signal processing in accordance with the methods described herein. In general, it will be recognised that processer may comprise a number of control or processing modules for controlling one or more features of the method and may also include one or more storage elements, for storing desired data, e.g., oscillation parameters, buffered signals, etc. The modules and storage elements can be implemented using one or more processing devices and one or more data storage units, which processing devices and/or storage devices may be at one location or distributed across multiple locations and interconnected by one or more communication links. Processing devices may include desktop computers, laptop computers, tablets, smartphones, personal digital assistants and other types of devices, including devices manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

Figure 4:
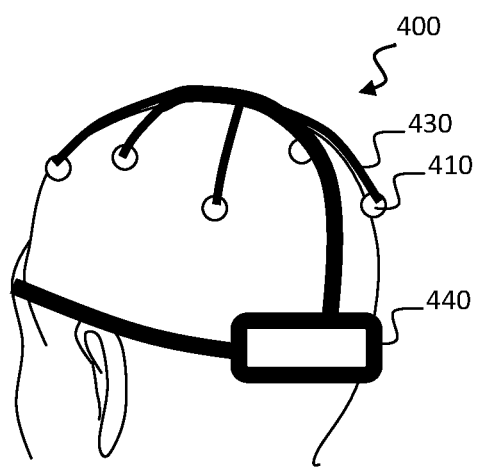
FIG. 4 is a rear view of a headset according to an embodiment of the present disclosure.

The apparatus can be deployed for use adjacent the head of a patient in a number of configurations. In one embodiment, as illustrated in FIG. 4, the apparatus is deployed in a headset 400. The headset includes a plurality of electrodes 410 mounted on arms 420 that extend to desired points on a patient's head 430, and a base unit 440 that is connected to the electrodes 410 and includes the remaining circuitry. The headset 400, or other types of electrode apparatus, can be adapted to position electrodes adjacent some or all of the key regions of the brain including one or more of: the frontal region (including the prefrontal cortex); the parietal region; the occipital region; the temporal region and the cerebellum. This spread of electrodes may enable brain activity signals to be monitored at one or more targeted regions of the brain and/or for stimulation signals to be applied to one or more targeted regions of the brain. Moreover, the spread of electrodes may enable the location in the brain where certain brain activity signals are being induced to be determined ("pinpointed"). The spread of electrodes may also enable stimulation signals to be applied dynamically to multiple brain regions to couple or decouple brain activity between those regions in real time or decease or increase a degree of anti-correlational activity between those brain regions.

In alternative embodiments, the same principles as discussed above with reference to e.g., FIGS. 1 and 2 can be applied in relation to other types of stimulation signals and brain activity signals. For example, brain activity signals can include but are not limited to signals, or a combination of signals, obtained using Near infrared spectroscopy (NIRS), Magnetoencephalography (MEG), Electromyography (EMG), and/or Electrocardiography (ECG) and/or Functional magnetic resonance imaging (fMRI). Moreover, stimulation signals can include non-electrical signals, such as transcranial magnetic stimulation (tMS) signals. When the stimulation signal is a tMS signal, it is applied transcranially using a coil that locates adjacent the patient's scalp. While the stimulation signal 201 represented in FIG. 2 has a sinusoidal waveform, it may have other waveforms, e.g., square-wave, sawtooth, triangle-wave or otherwise.

The set of first oscillation parameters can comprise the frequency, phase and amplitude of the generated stimulation single. The one or more second oscillation parameters that are determined can comprise any one or more of the frequency, phase and amplitude of the oscillating modified activity signal. For example, in one embodiment the second oscillation parameters can comprise at least the frequency of the modified activity signal. In another embodiment, the second oscillation parameters can comprise at least the frequency and phase of the modified activity signal.

As discussed above, signal processing, identified at 270 in FIG. 2, for example, is used to identify one or more second oscillation parameters of the modified activity signal. Signal processing is also performed at 260 in relation to the subtraction of the feedback signal and thus removal of the signal artefact. The signal processing can include conditioning and/or alignment of the feedback signal prior to its subtraction from the brain activity signal. Signal processing can employ filtering techniques that are known in the art to isolate primary signal components, e.g., within frequency bands of interest and to remove secondary noise components. The primary components can be further processed to extract specific features of interest such as frequency, phase, amplitude or interactions therein. These and other features can be extracted from a data buffer of a signal of arbitrary length, continuously or in response to an external input, e.g. in accordance with discussions further below.

By determining a frequency of the modified activity signal, for example, a frequency of the stimulation signal can be adjusted, e.g., at 280 of FIG. 2, to have the same frequency as the modified activity signal (and generally, therefore, the endogenous brain activity). This can provide for entrainment of the endogenous oscillations at the frequency of stimulation.

Similarly, by determining a phase of the modified activity signal, for example, a phase of the stimulation signal can be adjusted, e.g., at 280 of FIG. 2, to have the same phase as or a desired phase-shift from, a determined phase of the modified activity signal. This can provide for intentional phase matching or mis-matching of the endogenous oscillations with the phase of stimulation. For example, the phase of the stimulation signal can be adjusted to be in-phase with the determined phase of the modified activity signal. Alternatively, the phase of the stimulation signal can be adjusted to be out of phase (e.g. anti-phase) with the determined phase of the modified activity signal.

It is understood, for example, that fronto-parietal coupling of stimulation and neural activity signals in the theta band when in-phase (~0° relative phase) may be associated with recognition, encoding, short-term retention, and planning. In-phase synchronization can result in improved reaction times to the stimulation signal while out-of-phase desynchronization can result in a deteriorated performance. Nevertheless, out-of-phase desynchronization can still have valid therapeutic uses.

The brain activity signal and/or the modified activity signal can be filtered into one or more frequency bands prior to carrying out the signal processing to determine the one or more second oscillation parameters, e.g. at 270 of FIG. 2. The one or more second oscillation parameters can be determined for at least one of the frequency bands.

The stimulation signal can comprise one or more frequency bands and adjusting the set of first oscillation parameters of the stimulation signal based on the one or more second oscillation parameters of the modified activity signal that are determined can comprise adjusting the set of first oscillation parameters in at least one frequency band that corresponds to a frequency band in which the second oscillation parameters were determined. Adjusting the set of first oscillation parameters of the stimulation signal can comprise adjusting one or more of the first oscillation parameters.

The frequency bands can comprise one or more of: delta frequency band (<about 4 Hz), theta frequency band (about 4 to 8 Hz), alpha frequency band (about 8 to 14 Hz), beta frequency band (>about 14 Hz) and sub-bands and overlapping bands thereof, including gamma frequency band (>about 30 Hz) and Mu frequency band (about 8 to 12 Hz), or otherwise.

As indicated, the oscillation parameters can comprise frequency and phase. Thus, an alpha frequency of the stimulation signal can be adjusted to have the same frequency and/or phase as an alpha frequency of the modified activity signal, or a theta frequency of the transcranial stimulation signal may be adjusted to have the same frequency and/or phase as theta frequency of the oscillating activity signal, etc.

Within one or more frequency bands of interest, the generation and adjusting of the stimulation signal may be matched and optimised for a best fit with the endogenous brain activity of the patient, e.g., by having a corresponding frequency and/or phase to the modified activity signal. The generation of a stimulation signal with an appropriate fit may be carried out over a period of time, e.g. iteratively. For each iteration of a stimulation signal, a statistical index of the quality of fit may be calculated. Once the quality of fit is calculated to be sufficiently close and the stimulation signal is therefore generated, the method/apparatus may wait until the phase of the determined stimulation signal is aligned as desired with the endogenous oscillating signal and then a trigger may be provided, at that exact point in time, for the stimulation signal to be applied to the patient. The desired alignment of phase may be in-phase alignment or anti-phase alignment, for example. In-phase alignment of the stimulation signal with the endogenous activity offers a theoretically additive process potentially amplifying activity at a target frequency and/or region, while anti-phase alignment will suppress activity at the target frequency and/or region. The present disclosure describes a method and apparatus for directly modulating and steering activation patterns of oscillatory activity in the brain towards a desired outcome such as modulating mood and/or behaviour.

By basing the frequency and/or phase of the first parameters of the stimulation signal on corresponding parameters of the modified activity signal from the patient, a bespoke, patient-specific stimulation strategy can be determined in a closed-loop, realtime, environment. The approach may provide for dynamic changes in the stimulation strategy by continuously cycling through the above steps over an extended period of time. The stimulation strategy may be carried out until a desired therapeutic outcome is realised or until a predetermined total time has elapsed or otherwise.

The approach of the present disclosure can account for different cognitive functions being associated with neuronal activity across multiple, different frequency bands, and account for the optimal 'pattern' of activity being dependent on the individual patient and this changing over time. This can contrast with an approach where appropriate oscillation parameters for stimulation are determined 'off-line' and stimulation is provided in a fixed or static manner. The approach of the present disclosure can provide for frequency-coupling between the stimulation signal and the endogenous oscillating activity of the patient in one or more frequency bands.

Figure 5:
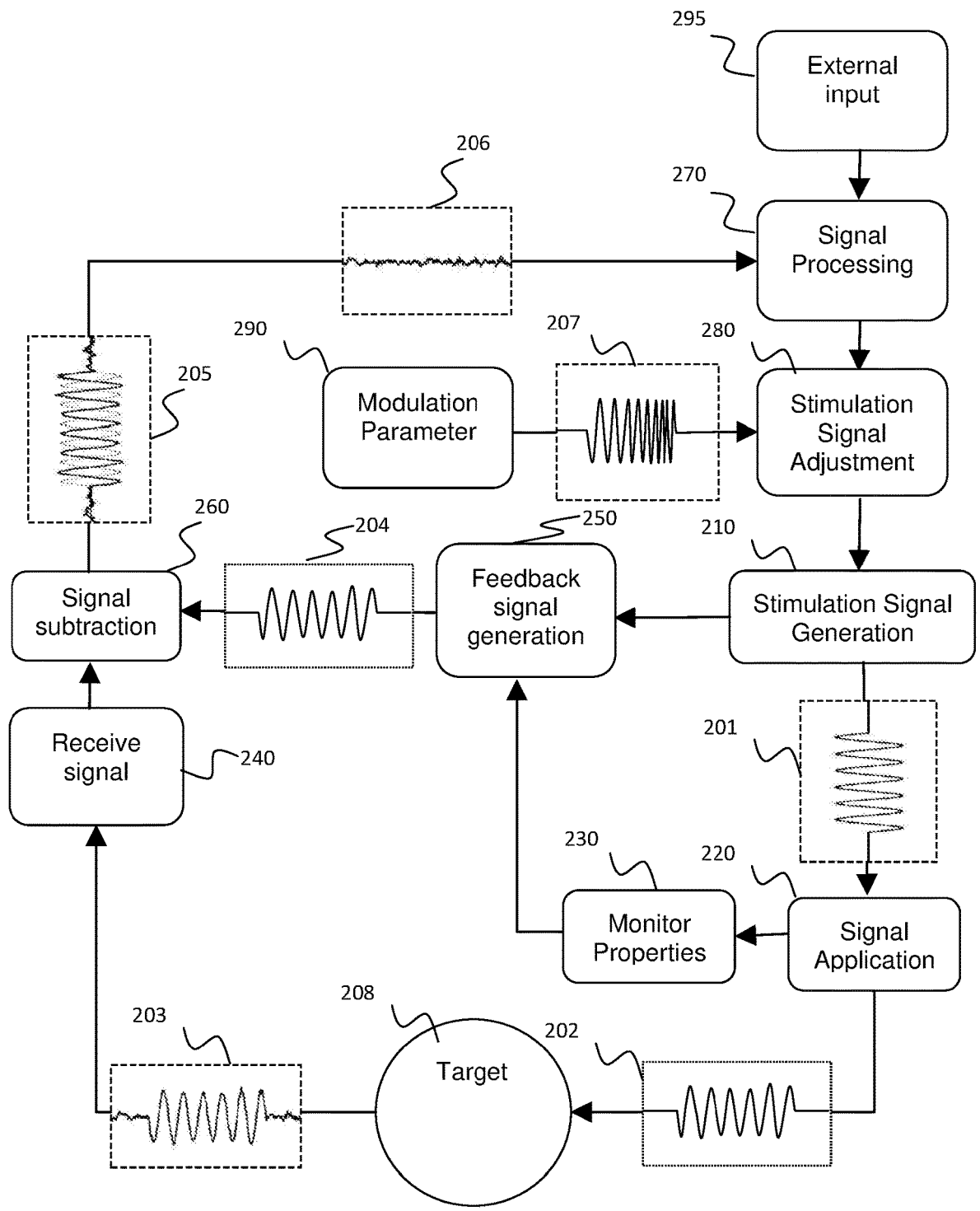
FIG. 5 is a modified version of the schematic diagram of FIG. 2 in accordance with an embodiment of the present disclosure.

In one embodiment, as shown in the schematic diagram of FIG. 5, which is a modified version of the schematic diagram of FIG. 2, the adjusting 280 of the set of first oscillation parameters of the stimulation signal can be based on a modulation parameter 290, in addition to the one or more second oscillation parameters that are determined. The modulation parameter may be a chirp, for example, with a modifying chirp signal being identified in box 207, for example. Thus, during application of the stimulation signal, the frequency of the stimulation signal may be increased (up-chirp) or decreased (down-chirp). Chirping of the stimulation signal may be reflected in the oscillating activity signals of the brain due to neural entrainment, i.e. the oscillation parameters of the activity signals of the brain may adjust to synchronise with the changing parameters of the stimulation signal.

In the embodiment of FIG. 5, an external input 295 is also provided that is configured to control protocols of the signal processing. The external input can be provided based on a task provided to the patient and/or based on an external observation of the patient's behaviour or environment. Where the external input is based on a task, the external input can be based on the commencement of the task and/or the patient's approach to completing the task, for example. Where the external input is based on an external observation, the external input can be based on facial expressions or biologic parameters of the patient indicative of mood, for example. The external input can cause a particular portion of the modified activity signal to be targeted for signal processing in order to generate the stimulation signal. The portion may be a specific time portion of the activity signal (e.g. corresponding to when the task was commenced or completed, etc.) and/or may be a portion having particular oscillation parameters, e.g. falling within a particular frequency band, for example. The external input can also trigger the commencement of the signal processing.

Figure 6:
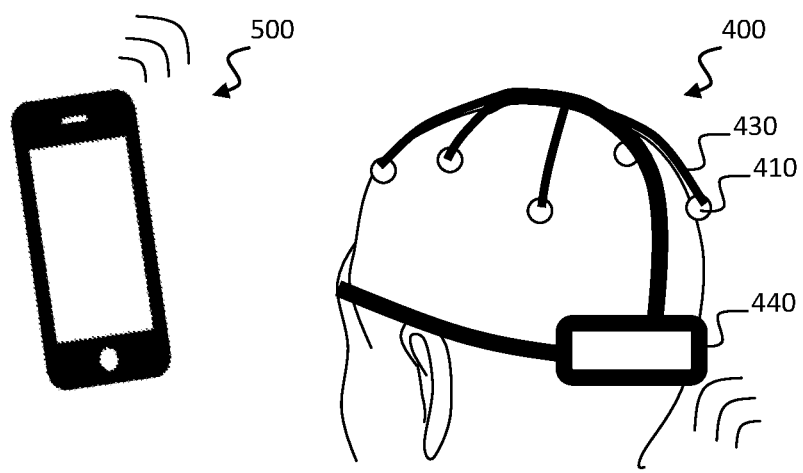
FIG. 6 is a rear view of the headset of FIG. 4 in communication with a personal computing device, in accordance with an embodiment of the present disclosure.

With reference to FIG. 6, in one embodiment, the external input is provided by an external device and, more specifically, a personal computing device 500 such as a smartphone or tablet. The personal computing device 500 is configured to communicate with the processor in the head set 400 as described above with reference to FIG. 4. Communication can be via wire or wirelessly, e.g., via Bluetooth® or WiFi®. The personal computing device 500 can set tasks for the patient, monitor completion of the tasks, and/or provide an external observation of the patient or the patient's environment. As an alternative to using a personal computing device such as a smartphone or tablet, a virtual or augmented reality device may be employed.

Thus, cognitive tasks, sensory stimuli, or combinations thereof can be incorporated in the control loop of the present disclosure, whereby performance on or an activated response to certain activities or events, for example, are used to inform and manipulate the generation of parameters of the stimulation signal. Due to the closed loop nature of the approach, endogenous activity can therefore be directly modulated during the execution of a specific task, by a specific individual towards optimal performance, for example.

Figure 7:
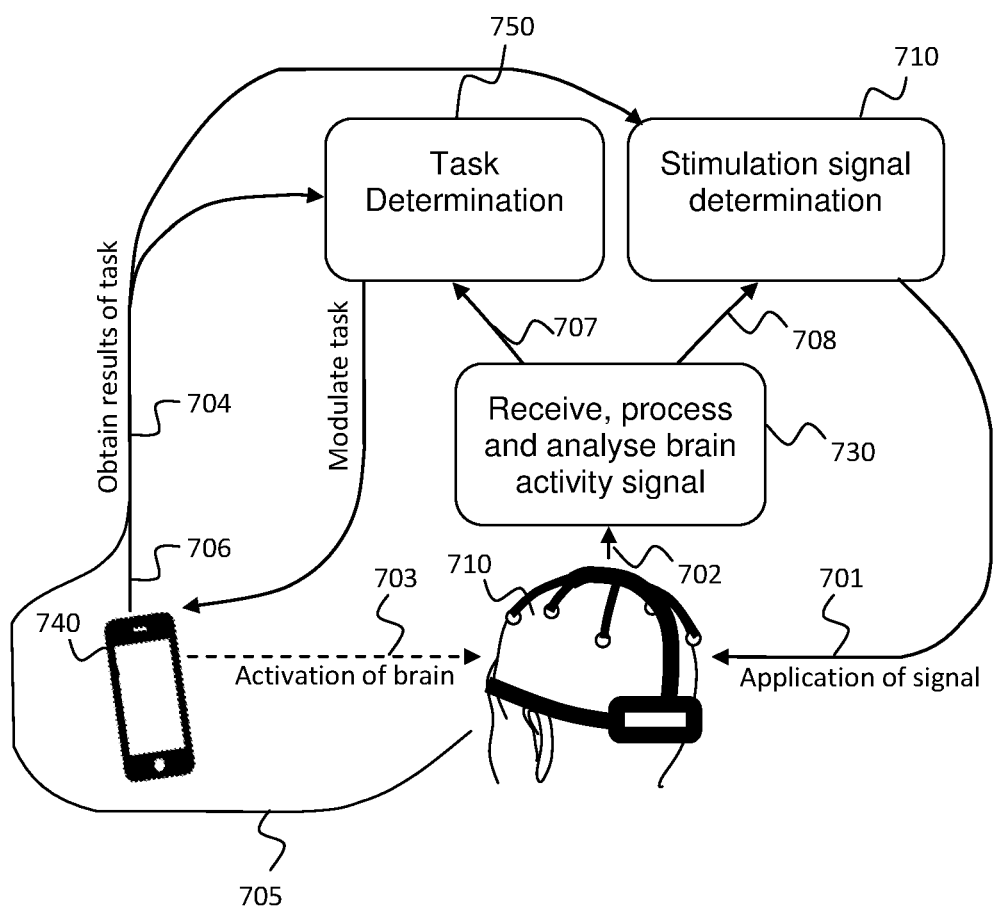
FIG. 7 is a flow chart illustrating a method of performing transcranial stimulation according to an embodiment of the present disclosure.

An embodiment of the present disclosure, in which a cognitive task process is carried in combination with a brain stimulation and monitoring process, is now described with reference to the flow chart of FIG. 7. A stimulation signal having a set of oscillation parameters is determined and generated 710. The stimulation signal is applied transcranially to the brain 701. A brain activity signal 702 from the brain is received, processed and analysed 730. In this step 730, a stimulation artefact can be removed from the brain activity signal, e.g., in accordance with techniques described with respect to one of more of the preceding embodiments (e.g. with reference to FIGS. 2 and 5), to obtain a modified activity signal. Artefact removal from the brain activity signal can result in a signal that is more closely aligned with endogenous oscillating activity signals in the brain of the patient 710. The modified activity signal is analysed, e.g., across two or more frequency bands of the modified activity signal.

In the cognitive task process, a cognitive task is presented to the patient 710 by an external device 740 such as a personal computing device, e.g., a smartphone or tablet, or otherwise. The carrying out of the task by the patient causes activation 703 of the patient's brain. Thus, the brain can be stimulated by both carrying out the task and by the applied transcranial stimulation signal 701, each of which can cause changes to the brain activity signal 702 as monitored.

During and/or following completion of the task, task results are obtained 704. Task results are obtained by monitoring a passive behaviour 705 and/or active behaviour 706 of the patient. Passive behaviour 705 can be monitored by making an external observation of the patient, e.g. by monitoring facial expressions or biologic parameters of the patient indicative of mood, for example. Active behaviour 706 can be monitored by recording deliberate reactions from the patient, e.g. that are inputted to the external device 740, or to one or more additional devices.

The task presented to the patient can be a passive or an active task. As an example, in a passive task, the patient may be asked to observe a video, a series of pictures or otherwise, without requiring any deliberate reaction from the patient. In contrast, in an active task, the patient may be asked to observe a video, a series of pictures or otherwise and provide a recordable, deliberate reaction e.g. by pressing a button and/or a point on a screen, for example. The deliberate reaction may provide a gauge of the patient's mood, e.g. where the patient is required to rate one or more of their emotions during or after the observation, for example.

As further examples of active tasks, the patient may be presented with one or more questions, interactive games or puzzles. The patient may provide a recordable, deliberate reaction (e.g. an answer) to the questions, interactive games or puzzles by pressing a button and/or a point on a screen, for example. The recordable reaction may provide a gauge of the patient's alertness, verbal or non-verbal reasoning capacity or otherwise. A specific example of an active task is a working memory task such as the "n-back" task, although a variety of other working memory tasks or other cognitive tasks may be used.

Where a passive task is carried out, monitoring of the patient's passive behaviour may be conducted only. Where an active task is carried out, monitoring of the patient's active and/or passive behaviour may be conducted.

Referring again to FIG. 7, in the control process, a task determination 750 is made. The task determination may comprise modulation of a task presented to the patient. The task presented to the patient can be modulated, at least in part, on the basis of the results 704 of the task. Additionally or alternatively, the task presented to the patient can also be modulated, at least in part, on the basis of the analysis of the modified activity signal 707. For example, on the basis of the results of the task and/or the modified activity signal, it might be determined that the task is too easy for the patient and the difficulty of the task may therefore be increased, or it might be determined that the task is too hard for the patient and the difficulty of the task may therefore be decreased. As another example, on the basis of the results of the task and/or the activity signal, it might be determined that the task is over-emotive for the patient and the emotive nature of the task may be reduced, or it might be determined that the task is under-emotive for the patient and the emotive nature of the task may be increased. Thus, a dynamic adjustment of the task may be carried out based on the results of the task and/or the modified activity signal. The adjustment can be carried out in real time due to the closed-loop nature of the approach described.

As discussed, as part of the process a stimulation signal is determined 710. The determination of the stimulation signal includes determining an adjustment to the oscillation parameters of the stimulation signal. In this embodiment, the stimulation signal applied to the patient 701 is adjusted, in part, on the basis of the results of the task 704. The stimulation signal applied to the patient is also adjusted, in part, on the basis of the analysis of the modified activity signal 708. On the basis of the results of the task and/or the modified activity signal, it may be determined that the task is difficult for the patient and an increased or adjusted stimulation is required to assist the patient with carrying out the task, or that the task is easy for the patient and a reduced or adjusted stimulation is appropriate. As another example, on the basis of the results of the task and/or the modified activity signal, it may be determined that the task is over-emotive for the patient and an increased or adjusted stimulation is required to assist the patient with coping with the task, or that the task is under-emotive and a reduced or adjusted stimulation is appropriate. Thus, a dynamic adjustment of the stimulation signal may be carried out based on the results of the task and/or the modified activity signal. The adjustment can be carried out in real time due to the closed-loop nature of the approach.

Figure 8:
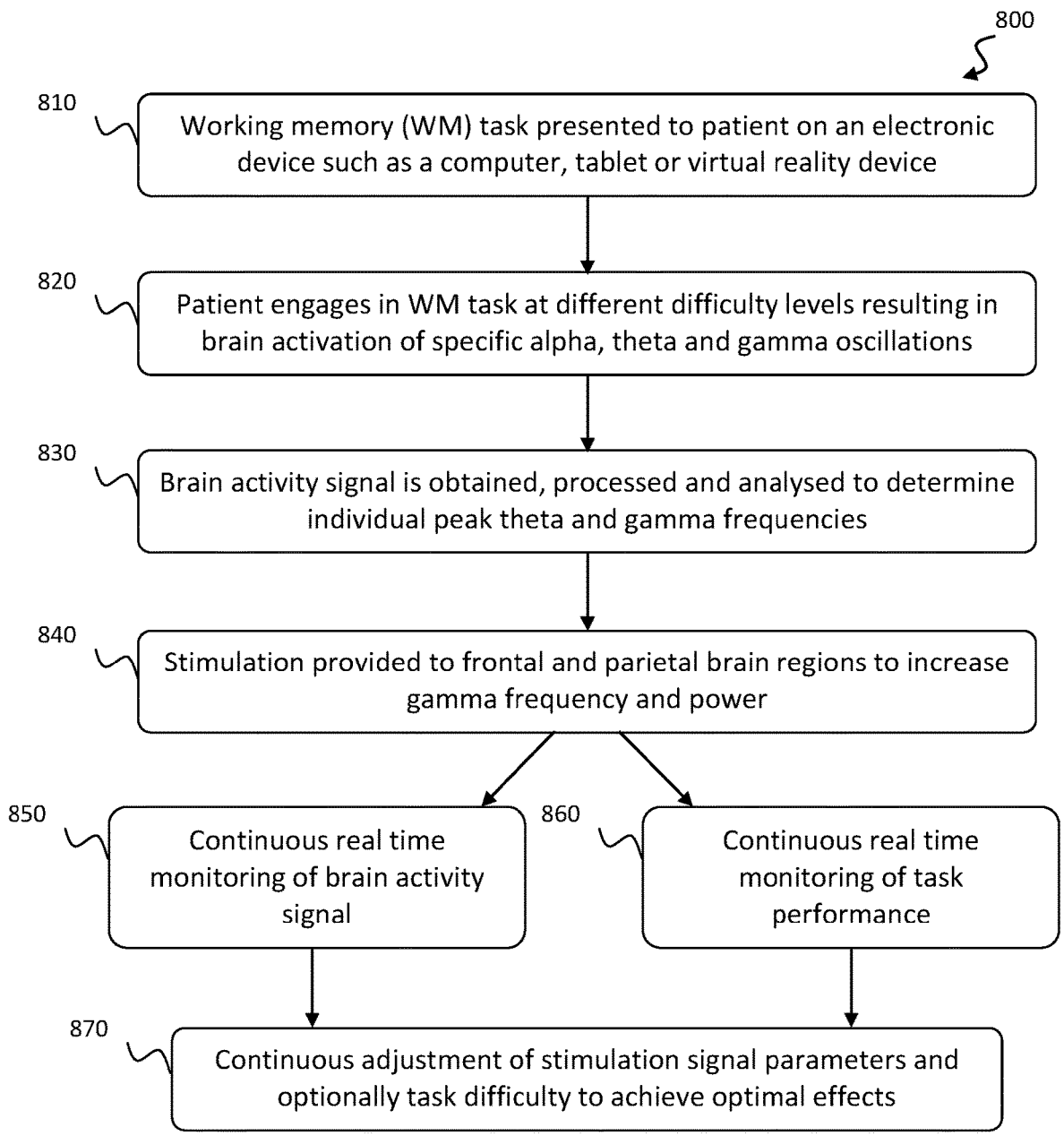
FIG. 8 is a flow chart illustrating another method of performing transcranial stimulation according to an embodiment of the present disclosure.

A specific example of a cognitive task monitoring and brain stimulation protocol, which can employ the control process described above with respect to FIG. 7, is now described with reference to the flowchart 800 of FIG. 8. The protocol is designed to alter or improve working memory (WM). Deficits of WM are seen in a diverse range of disorders including schizophrenia, depression, Parkinson's disease and Alzheimer's disease, and thus the approach may provide a method of treating one or more of these disorders.

At 810, while subject to transcranial brain stimulation, the patient is engaged in a cognitive task and specifically a working memory (WM) task. The WM task is presented via a computer platform such as a mobile device, tablet, desktop or laptop computer, or virtual reality head set. Examples of relevant WM tasks in this embodiment include the n-back working memory task and delayed match to sample tasks such as the Sternberg task. The task may be verbal or non verbal depending on the domain relevant to the patient (or may include both verbal and non verbal elements). The WM task can be embedded within a computer game or a game-like environment.

At 820, the patient engages in the task, resulting in the activation of specific brain regions and circuits. This will include the induction of oscillations in specific frequency bands. For example, during the retention phase of a WM task, it is known that an increase in alpha activity is typically seen. Moreover, there is also a specific pattern of theta and gamma oscillations such that a greater WM capacity is associated with lower theta and higher gamma activity.

At 830, while the patient continues to be engaged in the task, a brain activity signal is obtained, e.g. using EEG apparatus, and the signal is processed and analysed. Processing can include artefact removal, e.g. in accordance with embodiments described above, enabling real-time stimulation and monitoring. Various characteristics of the brain activity signal may be the focus of analysis, including the peak frequencies in specific frequency bands such as the alpha, theta and gamma frequency bands. The brain activity signal may also be analysed to determine information about the involvement of multiple brain regions in generating the relevant activity and/or to determine information about the anatomical sites of the generation of oscillations in specific frequency bands.

At 840, the transcranial stimulation, e.g. an electrical or magnetic transcranial stimulation signal such as tACS or tMS, is applied as a stimulation signal that is adjusted in view of the analysis of the brain activity signal at one or more specific frequencies. tACS may be applied differently across a combination of theta and gamma frequency bands. For example, the peak tACS frequency in the theta frequency band may be applied at a lower frequency, e.g. 1 Hz lower, than the recorded theta peak frequency of the brain activity signal and the peak tACS in the gamma frequency band may be applied higher, e.g. 1 Hz higher, than the recorded gamma peak frequency of the brain activity signal.

Meanwhile, at 850 and 860, continuous monitoring of the brain activity signal and the relevant task performance takes place in real time.

At 870, the oscillation parameters of the stimulation signal are adjusted based on the ongoing assessment of the brain activity signal and the relevant task performance. For example, the theta and gamma frequencies at which stimulation is applied may be adjusted progressively until predetermined peak frequencies in the respective frequency bands are achieved. Additionally or alternatively, the frequencies may be adjusted until a predetermined or dynamically determined level of task performance is achieved. Adjustments may also occur to alter the connectivity between brain regions in oscillatory frequencies or the site of the original activity. For example, stimulation parameters may be adjusted until there is a specific degree of frontal-parietal coherence in oscillatory activity. Also at 870, adjustment of the task difficulty may be carried out dynamically in the process, to ensure optimal induction of the relevant brain activity oscillations.

While stimulation and monitoring may be ongoing during task performance, in some embodiments, there may be discrete breaks in stimulation to assess the ongoing effects of the stimulation to the patient. Moreover, while the flowchart 800 of FIG. 8 starts with engagement of the patient in a cognitive task, in practice the flowchart may start at substantially any point due to the closed-loop nature of the approach.

Figure 9:
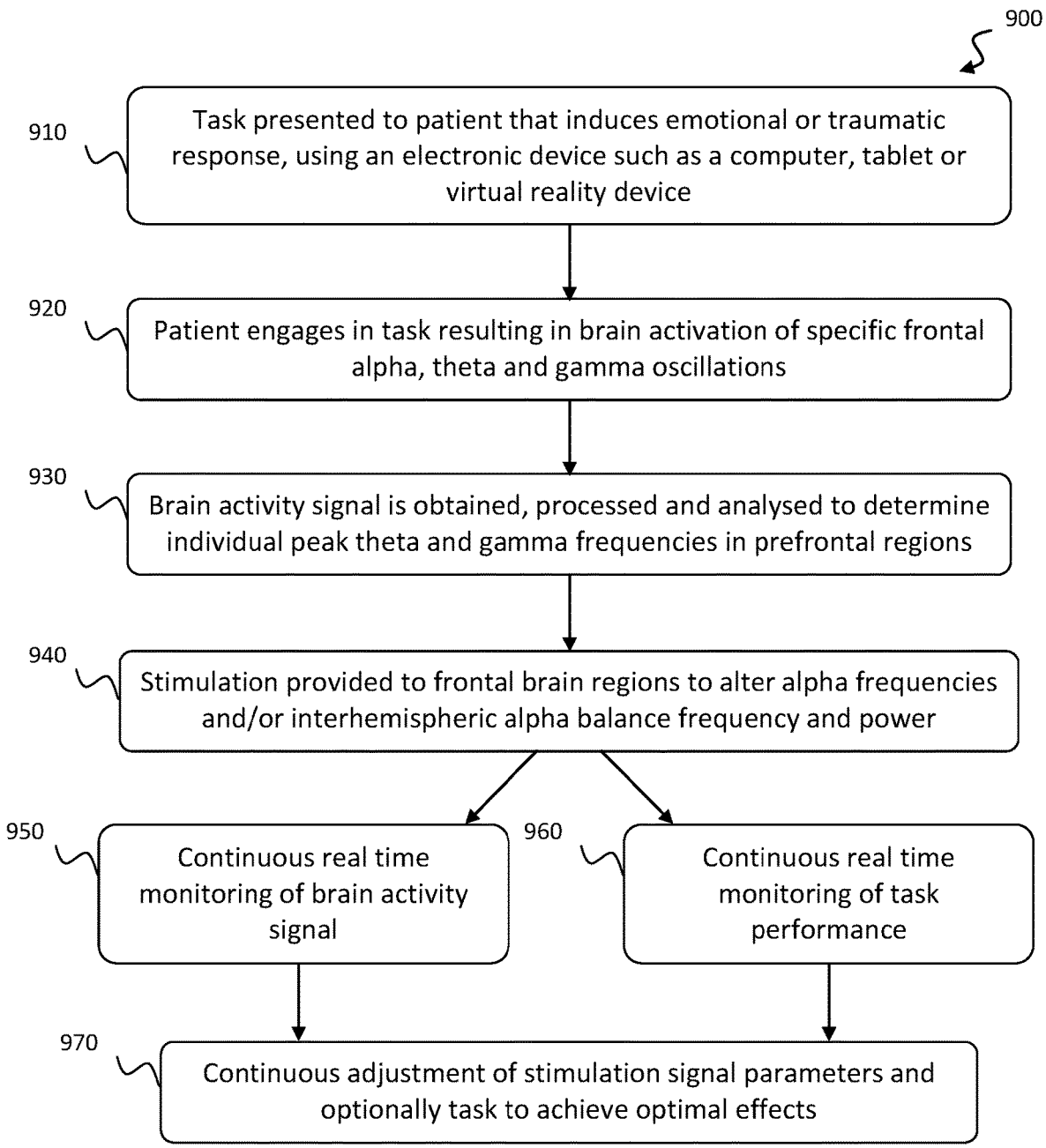
FIG. 9 is a flow chart illustrating yet another method of performing transcranial stimulation according to an embodiment of the present disclosure.

Another specific example of a cognitive task monitoring and brain stimulation protocol, which can employ the control methods described above with respect to FIG. 7, is now described with reference to the flowchart 900 of FIG. 9. The protocol may be similar to the protocol of FIG. 8, but modified for the treatment of anxiety disorders such as post-traumatic stress disorder (PTSD).

Following from this, in contrast to the previous example, rather than a WM task, the patient is presented with a task designed to activate emotional and/or traumatic responses from the patient. The task may be an affective priming task, an emotional induction task, an affective bias task or otherwise. When providing emotional and/or traumatic responses, the mid-line frontal (and parietal) theta activity of the patient can be expected to show excessive activation, for example.

Accordingly, upon presenting of the task to the patient (at 910), engagement of the task by the patient (at 920), and monitoring of the brain activity signal to recognize an emotional or traumatic response (at 930), a stimulation signal may be applied to relevant brain areas in the peak frequency of theta activation, such as the frontal brain regions (at 940). Stimulation may be applied anti-phase to the intrinsic oscillations to reduce oscillatory power. Continuous real time monitoring of the brain activity and task performance (at 950 and 960) can enable adjust of stimulation parameters that result in oscillatory power being reduced and frequency being adjusted to maintain the optimal conditions (at 970). For example, stimulation may be applied at a higher frequency (e.g. gamma) to shift oscillations away from the theta frequency band. Moreover, stimulation may be used to alter alpha frequencies and/or inter-hemishperical alpha balance.

Experimental Example 1

Cortical oscillating activity signals of patients were recorded using an EEG device in the following experimental paradigm: pre-stimulation resting phase for 2 minutes; listening/stimulating phase for 20 or 40 trials of 8 seconds listen followed by 8 seconds stimulate; post-stimulation resting phase for 2 minutes. An oscillating stimulation signal (tACS) was used with current 1-2 mA peak-to-peak, at instantaneous individual alpha frequency (IAF) (as measured in each listen period) and which was either in-phase or anti-phase with the subject's alpha oscillation. The effect of upregulating the frequency of the oscillating stimulation signal (up-chirp) or downregulating the frequency of the oscillating stimulation signal (down-chirp) was also examined.

Figure 10:
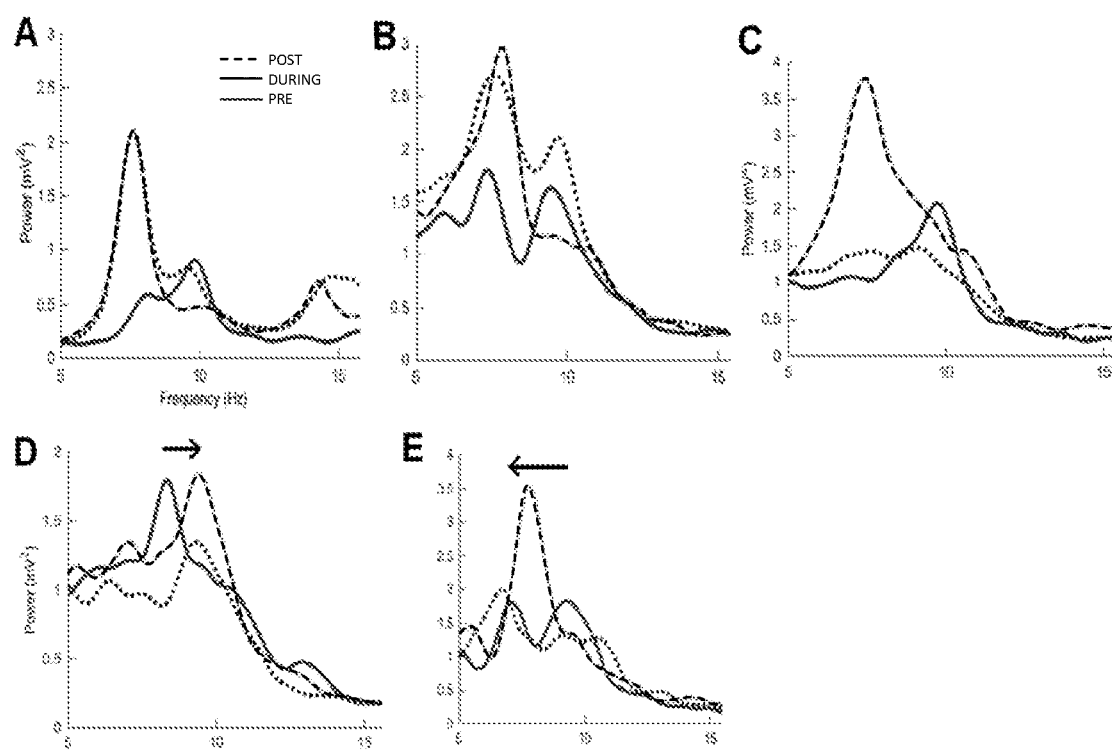
FIG. 10 shows graphs A to E, which illustrate EEG signals recorded pre-stimulation, during stimulation and post-stimulation in accordance with an example of the present disclosure.

In the graphs of FIG. 10, the EEG signals recorded pre-stimulation are represented using unbroken lines, which lines are therefore generally indicative of the endogenous oscillating activity signals of the subject. The EEG signals recorded poststimulation are represented using the dashed lines and the EEG signals recorded during stimulation are represented using the dotted lines. The EEG signals recorded during and post-stimulation are generally indicative of the changes to the endogenous oscillating activity signals as a result of stimulation.

Graphs A and B illustrate the effects on EEG recorded signals using two different stimulation intensities (1 mA and 2 mA, respectively) applied in-phase with the endogenous oscillating signals. In both cases there is clear entrainment of the endogenous oscillating activity signals at lower-alpha frequencies (e.g. <10 Hz), with the recorded oscillating activity signals during and post-stimulation having increased power at these frequencies.

Graph C illustrates the effect of using anti-phase stimulation (in comparison to the in-phase stimulation of Graphs A and B). As can be seen, there was little change in the power of the endogenous oscillating signals during the stimulation, albeit there was a large increase post-stimulation.

Graphs D and E illustrate the effect of applying a +1 Hz up-chirp (D) and a −1 Hz down-chirp to the stimulation signal that is initially at the endogenous frequency. When the up-chirp and down-chirp was applied, there was a corresponding clear shift in power as illustrated by the respective arrows in Graphs D and E.

Thus, the example illustrates that effective entrainment of endogenous frequencies, with evidence of modulation of the dominant frequency, is achievable in methods and systems according to the present disclosure.

Experimental Example 2

Cortical oscillating activity signals of patients were recorded by attaching a cathode and reference EEG electrode to a subject's the forehead, and an anode and reference EEG electrode to the posterior-occipital region. The subject was seated and in a relaxed state. tACS stimulation was delivered for 8 seconds at alpha frequency (10 Hz) ramping to 0.5 mA amplitude. The tACS stimulation signal was delivered in a constant current mode. The voltage signal amplitude fluctuated in accordance with small changes in subject scalp impedance in order to deliver the regular current sinusoid of fixed amplitude.

This voltage was digitized and monitored separately prior to amplification by the device, and was used to remove the artefact from the collected 'raw' EEG signal.

Figure 11A:
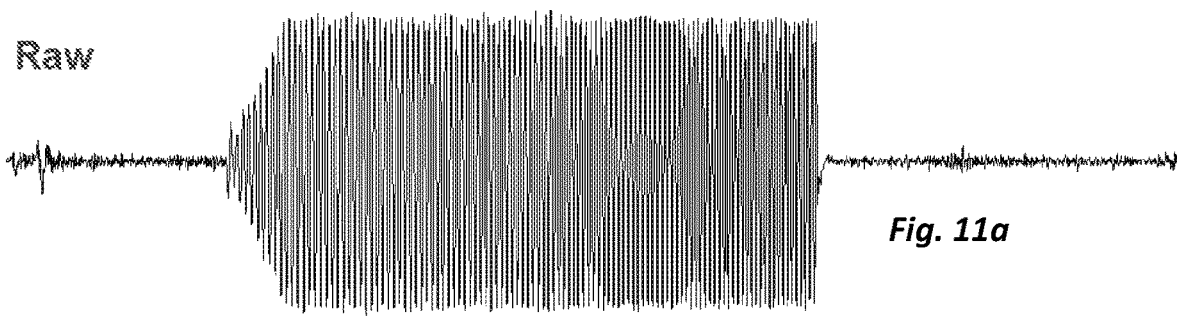
FIGS. 11a and 11b illustrate EEG signals before and after artefact removal, in accordance with an example of the present disclosure.
Figure 11B:
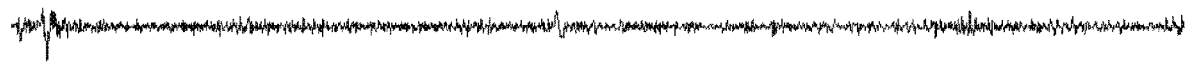

FIG. 11*a* represents the raw EEG signal prior to artefact removal and FIG. 11*b* represents the EEG signal with the artefact removed.

Thus, the example illustrates that effective removal of artefact signals is achievable in a closed-loop, 'real-time' stimulating and monitoring environment.

Apparatus for performing transcranial stimulation, the apparatus comprising circuitry configured to:
generate a stimulation signal having a set of first oscillation parameters;
apply the stimulation signal transcranially to a patient;
monitor the stimulation signal as applied to the patient;
receive a brain activity signal from the patient;
generate a feedback signal based on the monitored stimulation signal as applied to the patient; and
generate a modified activity signal by subtracting the feedback signal from the brain activity signal;
determine one or more second oscillation parameters of the modified activity signal; and
adjust the set of first oscillation parameters of the stimulation signal based on the one or more second oscillation parameters of the modified activity signal.

A method of performing transcranial stimulation comprising:
generating a stimulation signal having a set of first oscillation parameters;
applying the stimulation signal transcranially to a patient;
engaging the patient in a cognitive task:
receiving a brain activity signal from the patient;
monitoring a response of the patient to carrying out the task;
removing an artefact from the brain activity signal that is based on the stimulation signal, to obtain a modified activity signal;
analysing the modified activity signal;
adjusting the oscillation parameters of the stimulation signal as applied to the patient based on the response of the patient to carrying out the task and the analysis of the modified activity signal.

Optionally, the task results are received from an external device that presents the task to the patient.

Optionally, the task results are received from an external device that makes an external observation of the patient's behaviour or environment.

Optionally, the analysis of the modified activity signal is across two or more frequency bands of the modified activity signal and the adjustment of the oscillation parameters of the stimulation signal as applied to the patient is different for different frequency bands of the stimulation signal.

Optionally, the adjustment of the oscillation parameters for different frequency bands of the stimulation signal comprises increasing the peak frequency of the stimulation signal in one frequency band and decreasing the peak frequency of the stimulation signal in another frequency band.

Optionally, the adjustment of the oscillation parameters for different frequency bands is carried out until a predetermined or dynamically determined level of performance to carrying out the task is achieved by the patient.

Apparatus for performing transcranial stimulation, the apparatus comprising circuitry configured to:
generate a stimulation signal having a set of oscillation parameters;
apply the stimulation signal transcranially to a patient;
engage the patient in a cognitive task:
receive a brain activity signal from the patient;
monitor a response of the patient to carrying out the task;
remove an artefact from the brain activity signal that is based on the stimulation signal, to obtain a modified activity signal;
analyse the modified activity signal; and
adjust the oscillation parameters of the stimulation signal as applied to the patient based on the response of the patient to carrying out the task and the analysis of the modified activity signal.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of performing closed-loop transcranial stimulation comprising:
generating, by using a processor, a stimulation signal having a set of first oscillation parameters;
applying, by using two or more electrodes, the stimulation signal transcranially to a patient;
monitoring, by using the processor, the stimulation signal as applied to the patient to determine changes in voltage and/or impedance of the stimulation signal for taking into account an actual nature of the stimulation signal;
engaging the patient in a cognitive task;
receiving, by using the processor, a brain activity signal from the patient;
generating, by using the processor, a feedback signal based on the monitored stimulation signal as applied to the patient;
generating, by using the processor, a modified activity signal by subtracting the feedback signal from the brain activity signal, wherein the subtraction of the feedback signal from the brain activity signal removes an artefact from the brain activity signal that is based on the stimulation signal;
iteratively optimizing the stimulation signal for a fit with the modified activity signal and triggering the application of the stimulation signal upon alignment of a phase of the stimulation signal with a phase of the modified activity signal;
determining, by using the processor, one or more second oscillation parameters of the generated modified activity signal; and
receiving, by using the processor, an external input to control how the stimulation signal is adjusted based on the one or more second oscillation parameters and/or to control which of the one or more second oscillation parameters of the modified activity signal, generated by subtracting the feedback signal constructed in view of the monitoring of the stimulation signal, from the brain activity signal, are determined and/or when the one or more second oscillation parameters are determined, wherein the external input is based on a response of the task provided to patient.

2. The method of claim 1, wherein the alignment of the phase of the stimulation signal with the phase of the modified activity signal comprises an in-phase alignment.

3. The method of claim 1, wherein the alignment of the phase of the stimulation signal with the phase of the modified activity signal comprises an anti-phase alignment.

4. The method of claim 1, wherein the stimulation signal comprises a transcranial alternating current signal (tACS) that is delivered in a constant current mode, wherein a voltage of the tACS signal varies due to changes in impedance.

5. The method of claim 4, wherein one or more properties of the stimulation signal as applied to the patient are monitored, such as the voltage and/or impedance of the stimulation signal as applied to the patient.

6. The method of claim 1, wherein the set of first oscillation parameters comprise a frequency, phase and/or amplitude of the stimulation signal.

7. The method of claim 1, wherein the one or more second oscillation parameters that are determined comprise any one or more of frequency, phase and amplitude of the modified activity signal.

8. The method of claim 7, wherein adjusting the set of first oscillation parameters comprising adjusting at least one of:
a frequency of the stimulation signal to have the same frequency as the determined frequency of the modified activity signal; and
the phase of the stimulation signal to have the same phase as, or a desired phase-shift from, the determined phase of the modified activity signal.

9. The method of claim 8, wherein the phase of the stimulation signal is adjusted to have the same phase as the determined phase of the modified activity signal.

10. The method of claim 7, wherein adjusting the set of first oscillation parameters comprising adjusting the phase of the stimulation signal to have the same phase as, or a desired phase-shift from, the determined phase of the modified activity signal and adjusting a frequency of the stimulation signal to have the same frequency as the determined frequency of the modified activity signal.

11. The method of claim 1, wherein the brain activity signal and/or the modified activity signal is filtered into one or more frequency bands prior to determining the one or more second oscillation parameters, and wherein the stimulation signal comprises one or more frequency bands and adjusting the set of first oscillation parameters of the stimulation signal based on the one or more second oscillation parameters of the modified activity signal comprises adjusting the set of first oscillation parameters in at least one frequency band that corresponds to a frequency band in which the second oscillation parameters were determined.

12. The method of claim 11, wherein the frequency bands comprise one or more of: delta frequency band (<about 4 Hz), theta frequency band (about 4 to 8 Hz), alpha frequency band (about 8 to 14 Hz), beta frequency band (>about 14 Hz) and sub-bands and overlapping bands thereof, including gamma frequency band (>about 30 Hz) and Mu frequency band (about 8 to 12 Hz).

13. The method of claim 1, wherein the adjusting of the set of first oscillation parameters of the stimulation signal is based on a modulation parameter, in addition to the one or more second oscillation parameters that are determined, and wherein the modulation parameter is a chirp.

14. A method of performing closed-looped transcranial stimulation comprising:
   generating, by using a processor, a stimulation signal having a set of first oscillation parameters;
   applying, by using two or more electrodes, the stimulation signal transcranially to a patient;
   monitoring, by using the processor, the stimulation signal as applied to the patient to determine changes in voltage and/or impedance of the stimulation signal for taking into account an actual nature of the stimulation signal;
   engaging the patient in a cognitive task:
   receiving, by using the processor, a brain activity signal from the patient;
   monitoring, by using the processor, a response of the patient to carrying out the task;
   removing, by using the processor, an artefact from the brain activity signal that is based on the stimulation signal, to obtain a modified activity signal, wherein the removing of the artefact comprises determining a feedback signal and subtracting that feedback signal from the brain activity signal;
   iteratively optimizing the stimulation signal for a fit with the modified activity signal and triggering the application of the stimulation signal upon alignment of a phase of the stimulation signal with a phase of the modified activity signal;
   analysing, by using the processor, the modified activity signal and determining one or more second oscillation parameters;
   receiving, by using the processor, an external input to control how the stimulation signal is adjusted based on the one or more second oscillation parameters and/or to control which of the one or more second oscillation parameters are determined and/or when the one or more second oscillation parameters of the modified activity signal, generated by subtracting the feedback signal constructed in view of the monitoring of the stimulation signal, from the brain activity signal, are determined, wherein the external input is based on a response of the task provided to the patient.

15. The method of claim 14, wherein the alignment of the phase of the stimulation signal with the phase of the modified activity signal comprises an in-phase alignment.

16. The method of claim 14, wherein the alignment of the phase of the stimulation signal with the phase of the modified activity signal comprises an anti-phase alignment.

17. The method of claim 14, wherein the monitoring of the response of the patient to carrying out the task is based at least partly on the analysis of the modified activity signal.

18. The method of claim 14, wherein the method comprises receiving task results derived from a particular behaviour or reaction of the patient to carrying out the task, and wherein the monitoring of the response of the patient to carrying out the task is based at least partly on an analysis of the task results.

19. The method of claim 18, wherein the task presented to the patient is modulated, at least in part, on the basis of the results of the task, and wherein the task presented to the patient is to be modulated, at least in part, on the basis of the analysis of the modified brain activity signal.

20. The method of claim 14, wherein the analysing the modified brain activity signal comprises determining which regions or anatomical sites of the patient's brain generated some or all components of the modified activity signal, and wherein the applying of the stimulation signal to the patient comprises applying the stimulation signal to one or more of the determined regions or anatomical sites.

* * * * *